US012672971B2

(12) United States Patent
Lu et al.

(10) Patent No.: US 12,672,971 B2
(45) Date of Patent: Jul. 7, 2026

(54) PERIPHERAL VASCULAR STENT AND PREPARaTION METHOD THEREOF AND APPLICATION THEREOF

(71) Applicant: POLYREY MEDICAL TECH.(SUZHOU) CO., LTD., Suzhou (CN)

(72) Inventors: Xinwu Lu, Suzhou (CN); Nie Tang, Suzhou (CN); Peng Qiu, Suzhou (CN); Kaichuang Ye, Suzhou (CN); Jinbao Qin, Suzhou (CN); Ruihua Wang, Suzhou (CN); Cheng Gao, Suzhou (CN); Peng Xie, Suzhou (CN)

( * ) Notice: Subject to any disclaimer, the term of this patent is extended or adjusted under 35 U.S.C. 154(b) by 735 days.

(21) Appl. No.: 17/616,694

(22) PCT Filed: Feb. 25, 2021

(86) PCT No.: PCT/CN2021/077792
§ 371 (c)(1),
(2) Date: Dec. 6, 2021

(87) PCT Pub. No.: WO2022/178740
PCT Pub. Date: Sep. 1, 2022

(65) Prior Publication Data
US 2023/0172731 A1     Jun. 8, 2023

(51) Int. Cl.
*A61F 2/89* (2013.01)
*A61F 2/915* (2013.01)

(52) U.S. Cl.
CPC ...... *A61F 2/89* (2013.01); *A61F 2002/91575* (2013.01)

(58) Field of Classification Search
CPC .................. A61F 2/89; A61F 2002/072; A61F 2210/0076; A61F 2240/001;
(Continued)

(56) References Cited

U.S. PATENT DOCUMENTS 5,123,917 A * 6/1992 Lee ........................... A61F 2/86
623/1.42
5,810,872 A * 9/1998 Kanesaka ................. A61F 2/91
606/198

(Continued)

FOREIGN PATENT DOCUMENTS

CN         101909545 A    12/2010
WO      WO-2009089055 A1 *  7/2009    ............... A61F 2/07

*Primary Examiner* — Sarah W Aleman
*Assistant Examiner* — Rachel S Highland

(57) ABSTRACT

The peripheral vascular stent comprises scaffolding holding units and a membrane, each scaffolding holding units is formed of a closed ring shape wire; the membrane is covered on scaffolding holding units, the flexibility of the membrane is greater than that of the scaffolding holding units, between the wires of the same scaffolding holding unit and/or between two adjacent scaffolding holding units is provided a plurality of hollowed-out areas on the membrane, and two adjacent scaffolding holding units are only connected by the membrane beyond the hollowed-out areas. The peripheral vessel stent can meet the mechanical performance requirements, has a proper radial support force and good flexibility, and can well reduce the in-stent chronic external expansion force, has the advantages of little impact on blood flow, little injury to the vascular wall, and less likely to cause secondary thrombosis.

18 Claims, 5 Drawing Sheets

(58) Field of Classification Search
　　　CPC ...... A61F 2250/0018; A61F 2250/0029; A61F
　　　　　　　　　　　　2002/91575; A61F 2002/828; A61F
　　　　　　　　　　　　　　　　2002/91541; A61F 2/915
　　　USPC ........................................................ 623/1.16
　　　See application file for complete search history.

(56) References Cited

U.S. PATENT DOCUMENTS

| | | | | |
|---|---|---|---|---|
| 5,843,166 A * | 12/1998 | Lentz | ......................... | A61F 2/07 |
| | | | | 623/1.13 |
| 6,352,552 B1 * | 3/2002 | Levinson | ................ | A61F 2/915 |
| | | | | 623/1.15 |
| 7,316,710 B1 * | 1/2008 | Cheng | ....................... | A61F 2/91 |
| | | | | 623/1.15 |
| 7,560,006 B2 * | 7/2009 | Rakos | ....................... | A61F 2/06 |
| | | | | 156/287 |
| 8,696,733 B2 * | 4/2014 | Bogert | .................... | A61F 2/915 |
| | | | | 623/1.13 |
| 2005/0222667 A1 * | 10/2005 | Hunt | ......................... | A61F 2/07 |
| | | | | 623/1.13 |
| 2008/0300674 A1 * | 12/2008 | Jang | .......................... | A61F 2/91 |
| | | | | 623/1.15 |
| 2009/0005856 A1 * | 1/2009 | Pappas | .................... | A61F 2/915 |
| | | | | 623/1.16 |
| 2010/0298921 A1 * | 11/2010 | Schlun | ...................... | A61F 2/91 |
| | | | | 623/1.2 |
| 2015/0265438 A1 * | 9/2015 | Hossainy | .............. | A61L 31/041 |
| | | | | 623/1.11 |
| 2016/0015538 A1 * | 1/2016 | Kariniemi | ................ | A61F 2/07 |
| | | | | 156/187 |
| 2016/0296354 A1 | 10/2016 | Igaki et al. | | |

\* cited by examiner

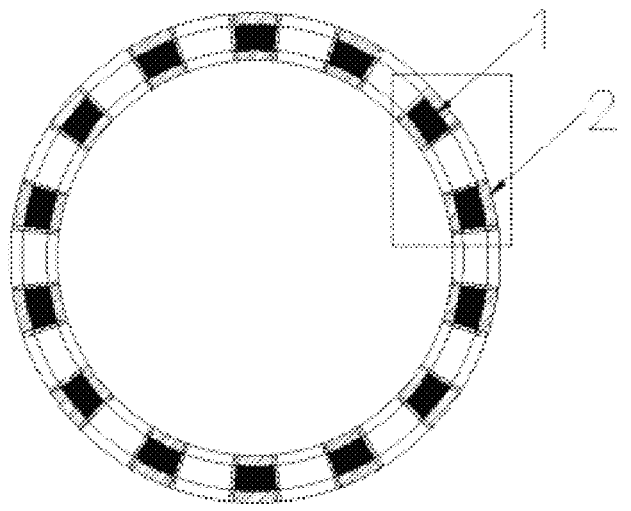
Figure 4
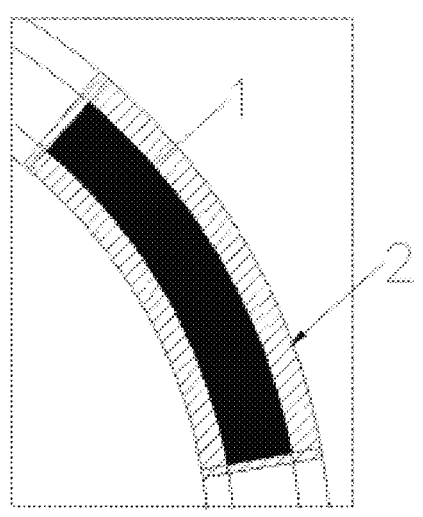
Figure 5
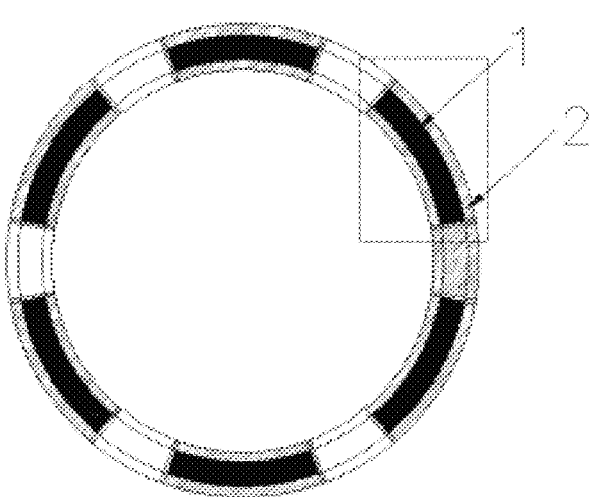
Figure 6
Figure 7

PERIPHERAL VASCULAR STENT AND PREPARaTION METHOD THEREOF AND APPLICATION THEREOF

RELATED APPLICATIONS

The present application is a U.S. National Stage Application of International Application Number PCT/CN2021/077792 filed Feb. 25, 2021, the disclosures of which are hereby incorporated by reference herein in their entireties.

TECHNICAL FIELD OF THE INVENTION

The present disclosure relates to the technical field of medical equipment, and in particular to a peripheral vascular stent and a preparation method thereof and an application thereof.

BACKGROUND OF THE INVENTION

The lower extremity arteriosclerosis obliterans (peripheral artery disease, PAD) caused by atherosclerosis is the third atherosclerotic cardiovascular disease after coronary heart disease and cerebral stroke. More than 300 million people worldwide suffer from PAD, and the evolution of the disease will cause claudication, resting pain, and amputation, which will seriously affect the quality of life of patients. The treatment methods of PAD mainly include drugs, open surgery and endovascular therapy. With the development of endovascular therapy for PAD, endovascular therapy has been shown to have less trauma and better curative effect, which has become the main way to treat PAD. The two most common methods of endovascular intervention are percutaneous transluminal angioplasty and endovascular stent implantation. The shortcoming of the former is that the 1-year patency rate is only 28%-37%, while the emergence of the latter significantly improves the short- and long-term patency rate of the lesion vessels.

At present, the commonly used vascular stents are mainly divided into two categories: cut type and braided type, the braided stent is mainly woven by metal wires, while the cut stent includes multiple closed rings spaced apart in the axial direction and made of metal material, and metal connection piece that connects two adjacent closed rings. Wherein, the braided stent has a certain degree of flexibility and fatigue resistance, but its axial shortening rate is very high and its smaller axial shortening rate, but its flexibility is poor.

In addition, the lower extremity arteries of the human body have unique physiological characteristics, pathological characteristics, kinematics characteristics, hydrodynamic characteristics, etc., but the existing peripheral arterial stents cannot fully meet the unique requirements of the lower extremity arteries, and after stent treatment, more than about 40% of patients with lower extremity arterial disease will induce in-stent restenosis due to chronic external expansion force of stent and low in-stent shear force. Peripheral arterial stents need to overcome mechanical factors such as chronic external expansion force and low shear force while ensuring a certain radial support force, however, none of the existing peripheral arterial stents can meet this requirement, which is the main reason for the high re-intervention rate after peripheral arterial stent implantation.

SUMMARY OF THE INVENTION

A technical problem to be solved by the present disclosure is to provide a vascular stent with sufficient radial support force and good flexibility, which can be applied to peripheral vessels.

The second technical problem to be solved by the present disclosure is to provide a method for preparing the above-mentioned vascular stent.

The third technical problem to be solved by the present disclosure is to provide an application of the above-mentioned vascular stent in endovascular treatment.

To achieve the above-mentioned purposes, the present disclosure employs the following technical schemes:

One aspect of the present disclosure provides a peripheral vascular stent having an expanded state and a contracted state, the peripheral vascular stent has a larger inner diameter in the expanded state than that in the contracted state; the peripheral vascular stent comprises:

scaffolding holding units, the scaffolding holding units are a plurality of scaffolding holding units arranged at intervals along an axial direction of the peripheral vascular stent, each of the scaffolding holding units is formed of a wire and is in a closed ring shape, and each of the scaffolding holding units comprises a plurality of peaks and valleys regularly arranged in the circumferential direction, with two adjacent peaks forming a cycle;

a membrane, the membrane is covered on the plurality of scaffolding holding units, the flexibility of the membrane is greater than that of the scaffolding holding units, the membrane between the wires of the same scaffolding holding unit and/or between two adjacent scaffolding holding units is provided a plurality of hollowed-out areas, and two adjacent scaffolding holding units are only connected by the membrane beyond the hollowed-out areas.

Because the lower extremity arteries are different from other fixed arteries (such as coronary arteries, carotid arteries, aorta), they are in various deformed states under the movements of the lower extremities for a long time, for example, the popliteal artery in the gardening posture: the shortening rate is 13%-25%, the radius of curvature after bending is 8-17 mm, and the maximum twist is 14-26°/cm. These artery deformations after movement will cause radial compression, torsion, bending, axial stretching and compression of the stent, and the existing peripheral vascular stents are limited to the homogeneous design, so the flexibility and support force of the material cannot be considered at the same time, so it cannot satisfy the characteristics of the lower extremity arteries mentioned above at the same time. The vascular stent of the present disclosure surpasses the limitation of homogeneous design, has no metal connection between the plurality of scaffolding holding units in the stent, and the connection is only made through a flexible membrane with the hollowed-out areas, and in the first aspect, the flexible structural connection has no fatigue damage of the metal connection structure, and the flexible structure is less irritating to endothelial cells during the shortening process, thereby reducing vascular injury, and can adapt to the shortening rates of the artery in various deformed states; in the second aspect, the vascular stent with the structure of the present disclosure can meet the challenges of the deformation of the peripheral vessels under torsion, and the flexible structure has little irritation to endothelial cells during the torsion process, thereby reducing vascular injury; in the third aspect, the vascular stent of the present disclosure has no "fish-scale effect" or fatigue damage in the metal stent during limb flexion, especially in the peripheral vessels of the knee joint (such as the popliteal artery, etc.), and the present disclosure can achieve bending under a small radius of curvature without injuring the vascular endothelium; in the fourth aspect, since the vascular stent of the structure of the present disclosure adopts a flexible connection, there is a sufficient axial stretching rate to meet the axial stretching deformation of the peripheral vessels; and in the fifth aspect, the vascular stent of the present disclosure adopts a plurality of closed annular scaffolding holding units arranged at intervals in the axial direction, so it can provide sufficient radial support force and can withstand the radial force and collapse or pinch load of peripheral vessels, effectively support the artery and provide sufficient blood flow.

According to some specific and preferred implementations, between two adjacent scaffolding holding units, one scaffolding holding unit and the other scaffolding holding unit are staggered on the circumferential surface, and the staggered distance is less than one-half cycle, so that the vascular stent has better bending, torsion, axial compression and stretching properties.

Further preferably, the staggered distance is less than or equal to a quarter of the cycle.

Further preferably, in a clockwise direction, each of the scaffolding holding units and the adjacent scaffolding holding unit are staggered on the circumferential surface and the staggered distance is the same, so that the scaffolding holding units can form a spiral-like structure as a whole, so that the vascular stent can better maintain the circular cross-section of the vascular stent in the state of bending, torsion, etc., and avoid the collapse of the vascular stent.

It should be noted that the clockwise direction herein is only for ease of description, and does not constitute a limitation on the scope of protection of this application, and when the direction is counterclockwise, the same technical effect can be achieved, which is also within the scope of protection of this application.

According to some specific and preferred implementations, the axis of each scaffolding holding unit coincides with the axis of the peripheral vascular stent. In this application, the axis line of each scaffolding holding unit coinciding with the axis line of the peripheral vascular stent means that when the peripheral vascular stent comprises a main stent and a sub-stent connected to the main stent, the axis line of the scaffolding holding units located in the main stent part coincides with the axis line of the main stent, and the axis line of the scaffolding holding units located in the sub-stent part coincides with the axis line of the sub-stent; when the peripheral vascular stent has no branches, the axis of each scaffolding holding unit coincides with the axis of the peripheral vascular stent.

According to some specific and preferred implementations, the hollowed-out areas comprise first hollowed-out portions located within the peaks of each scaffolding holding unit, second hollowed-out portions located within the valleys of each scaffolding holding unit, a plurality of third hollowed-out portions located between two adjacent scaffolding holding units and in communication with the first hollowed-out portions and the second hollowed-out portions respectively; thus, the vascular stent has better flexibility and can be better bent and twisted with the vessels.

In some implementations, parts of the plurality of third hollowed-out portions between two adjacent scaffolding holding units may be in communication with each other, but they cannot all be in communication with each other, resulting in no membrane connection between two adjacent scaffolding holding units and thus being separated.

Further, each of the third hollowed-out portions is only communicated with the nearest first hollowed-out portion and the nearest second hollowed-out portion, so that there are more connection positions between two adjacent scaffolding holding units, so that two adjacent scaffolding holding units are connected more firmly.

According to some specific and preferred implementations, between two adjacent scaffolding holding units, the valley bottoms of one scaffolding holding unit and the nearest peak tops of the other scaffolding holding unit are only connected by strip-shaped membranes.

According to some more specific and preferred implementations, the first hollowed-out portions are surrounded by first walls and second walls connected by upper ends thereof, and the second hollowed-out portions are surrounded by third walls and fourth walls connected by lower ends thereof, the third hollowed-out portions are surrounded by fifth walls respectively connected to the lower ends of the first walls and the upper ends of the fourth walls, and sixth walls respectively connected to the lower ends of the second walls and the upper ends of the third walls.

Further preferably, the first hollowed-out portions and the second hollowed-out portions are as large as possible, and it is only necessary to ensure that the membrane covers the scaffolding holding units, in addition, since two adjacent scaffolding holding units are staggered, the first hollowed-out portions and the second hollowed-out portions are also staggered, so that the hollowed-out areas form a plurality of two staggered and mirrored triangles, so that the vascular stent has better flexibility and can be better bent and twisted with the vessels.

Further preferably, when the peripheral vascular stent is split along its axial direction and spread into a plane shape, two nearest first walls of two adjacent scaffolding holding units are on a first straight line, and the first straight is arranged obliquely, so that the scaffolding holding units can form a spiral-like structure, so that the vascular stent can better maintain the circular cross-section of the vascular stent in the state of bending, torsion, etc., and avoid the collapse of the vascular stent.

Further preferably, angles between the first walls and the second walls are acute angles.

Further preferably, the first walls and the third walls are parallel, the second walls and the fourth walls are parallel, and a plurality of second walls are parallel.

According to some specific and preferred implementations, the membrane is wrapped on the outer side or/and inner side of the scaffolding holding units, so that the vascular stent of the present disclosure has less influence on the blood flow in the vessel, thereby reducing the incidence of blood flow disorder and abnormal shear stress/shear rate after stent implantation, thereby reducing the probability of a series of inflammation and vascular injury in the vessels. In addition, the present disclosure effectively increases the attached area of the vascular stent and the vessel by covering the scaffolding holding units with a softer membrane, thereby increasing the pull-out force of the vascular stent to the vessel, thereby further reducing the chronic external expansion force of the vascular stent while maintaining sufficient radial support force and good flexibility. Moreover, on the one hand, the membrane covering design can seal the interlayer crevasse of peripheral vessels to a certain extent; on the other hand, compared with the full-covering membrane design, the provision of the hollowed-out areas on the membrane can avoid completely covering the branch vessels, so that it is suitable for peripheral vessels with more branch vessels, such as the popliteal artery.

According to some specific and preferred implementations, the membrane comprises an inner membrane located on the inner side of the scaffolding holding units and an outer membrane located on the outer side of the scaffolding holding units, the inner membrane and the outer membrane are fixedly connected, and the scaffolding holding units are wrapped between the inner membrane and the outer membrane.

Further, the inner membrane and the outer membrane that are in contact are thermally melted to form the membrane.

According to some preferred implementations, the inner diameter of the peripheral vessel stent in the expanded state is gradually tapered from one end to the other end, so as to meet the physiological characteristics of the lower extremity arteries of the human body with a tapered diameter, effectively increase the attached area of the vascular stent to the blood vessel, and reduce the chronic external expansion force of the stent, thereby avoiding the probability of in-stent restenosis.

According to some specific and preferred implementations, the membrane is coated with drugs, thereby greatly increasing the drug attachment area and providing more drug attachment methods, and the drugs that can be coated on the surface of the membrane include, but are not limited to, drug polymers carriers or active agents (such as biologically active agents), and topically administrated therapeutic substances, to achieve anti-vascular proliferation and anti-endothelialization.

According to some specific and preferred implementations, the material of the scaffolding holding units is selected from the group consisting of stainless steel, memory alloy, titanium alloy, tantalum alloy, cobalt-chromium alloy, biodegradable metal, biodegradable polymer, magnesium alloy, pure iron, and combinations thereof, preferably nickel-titanium alloy.

According to some specific and preferred implementations, the material of the membrane is selected from the group consisting of polytetrafluoroethylene, polyether block amide, polyimide, bioabsorbable medical materials, and combinations thereof, preferably, the membrane is polytetrafluoroethylene microporous membrane.

The peripheral vessel stent of the present disclosure is suitable for endovascular treatment of various peripheral vessels including superficial femoral artery, iliac artery, carotid artery, radial artery, and lower extremity artery, etc. Wherein, the peripheral vessel stent of the present disclosure is particularly suitable for vessels that undergo large deformation.

The scaffolding holding units in the present disclosure may be self-expanding or balloon-expanding scaffolding holding units.

The second aspect of the present disclosure is to provide a method for preparing the peripheral vessel stent, wherein fixing the membrane and the scaffolding holding units with each other, and then opening a plurality of hollowed-out areas on the membrane.

The third aspect of the present disclosure is to provide a method for preparing the peripheral vessel stent, wherein opening a plurality of hollowed-out areas on the membrane, and then fixing the membrane and the scaffolding holding units with each other.

The fourth aspect of the present disclosure is to provide a method for preparing the peripheral vessel stent, respectively arranging an inner membrane and an outer membrane on the inner side and outer side of the scaffolding holding units, wrapping the scaffolding holding units between the inner membrane and the outer membrane by heating the inner membrane and the outer membrane, thermally melting the inner membrane and the outer membrane beyond the scaffolding holding units to form into an integral membrane, and then opening a plurality of hollowed-out areas on the membrane.

The fifth aspect of the present disclosure is to provide a method for preparing the peripheral vessel stent, respectively opening a plurality of hollowed-out areas on an inner membrane and an outer membrane, then respectively arranging the inner membrane and the outer membrane on the inner side and outer side of the scaffolding holding units, aligning the hollowed-out areas on the inner membrane with the hollowed-out areas on the outer membrane, wrapping the scaffolding holding units between the inner membrane and the outer membrane by heating, and thermally melting the inner membrane and the outer membrane beyond the scaffolding holding units to form into an integral membrane.

The sixth aspect of the present disclosure is to provide an application of the above-mentioned peripheral vascular stent in endovascular treatment.

Due to the use of the above technical solutions, the present disclosure has the following advantages over the prior art:

The peripheral vessel stent of the present disclosure can meet the mechanical performance requirements under various deformed states of peripheral vessels, the peripheral vessel stent of the present disclosure can made a compromise between proper radial support force and good flexibility, can well reduce the in-stent chronic external expansion force of the peripheral vessel stent, reduce the incidence of in-stent restenosis of the peripheral vessel stent, in addition the peripheral vessel stent of the present disclosure has the advantages of little impact on blood flow, little injury to the vascular wall, and less likely to cause secondary thrombosis.

BRIEF DESCRIPTION OF THE DRAWINGS

For more clearly explaining the technical solutions in the embodiments of the present application, the accompanying drawings used to describe the embodiments are simply introduced in the following. Apparently, the below described drawings merely show a part of the embodiments of the present disclosure, and those skilled in the art can obtain other drawings according to the accompanying drawings without creative work.

FIG. 4 is a sectional view taken along line A-A of FIG. 3;

FIG. 5 is a partial enlarged view of FIG. 4;

FIG. 6 is a sectional view taken along line B-B of FIG. 3;

FIG. 7 is a partial enlarged view of FIG. 6;

DETAILED DESCRIPTION OF EXEMPLARY EMBODIMENTS

In the following, only certain exemplary embodiments are briefly described. As those skilled in the art can realize, the described embodiments may be modified in various different ways without departing from the spirit or scope of the embodiments of the present disclosure. Therefore, the drawings and description are to be regarded as illustrative in nature and not restrictive.

Figure 1:
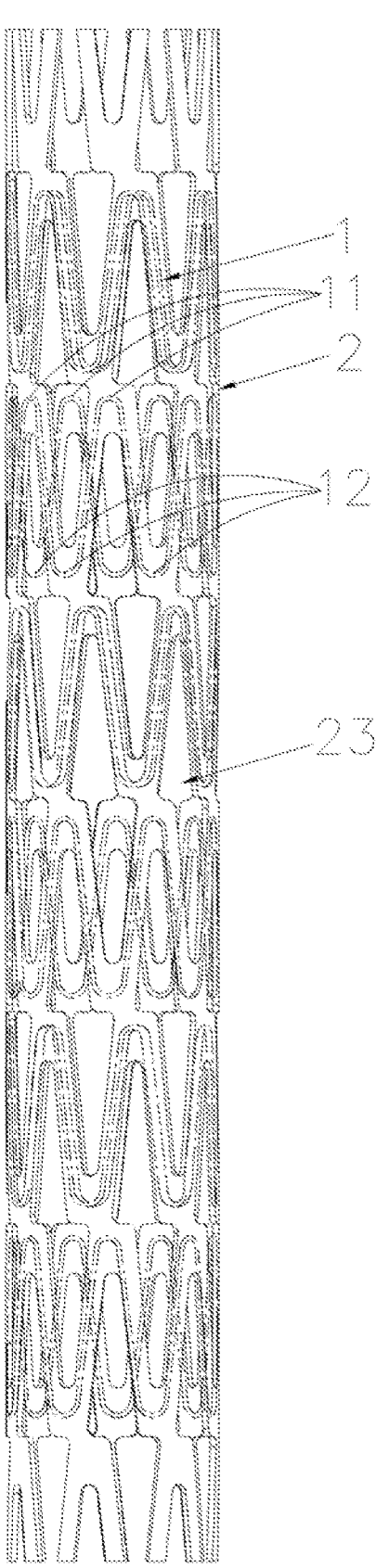
FIG. 1 is a three-dimensional view of a vascular stent provided in Embodiment 1 of the present disclosure.

In the description of the embodiments of the present disclosure, it should be understood that the orientation or position relation indicated by the terms "length", "inner", "upper" and the like are based on the orientation or position relation shown in FIG. 1, and are only for the convenience of describing the embodiments of the present disclosure and simplifying the descriptions, rather than indicating or implying that the pointed device or element must have a specific orientation, be configured and operated in a specific orientation, and therefore cannot be understood as a limitation to the embodiments of the present disclosure.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of the embodiments of the present disclosure, "a plurality of" means two or more than two, unless otherwise specifically defined.

In the embodiments of the present disclosure, unless otherwise clearly specified and defined, the terms "mount", "communicate", "connect", "fix" and other terms should be understood in a broad sense, for example, it may be a fixed connection, it can be a detachable connection, or integrated; it can be a mechanical connection, it can be an electrical connection, or it can be in communication; it can be directly connected, or indirectly connected through an intermediate medium, it can be an internal communication between two elements or an interaction relationship between two elements. For those of ordinary skill in the art, the specific meanings of the above-mentioned terms in the embodiments of the present disclosure can be understood according to specific conditions.

In the embodiments of the present disclosure, unless otherwise clearly specified and defined, the "above" or "under" of the first feature on the second feature may include that the first and second features are in direct contact, or may include that the first and second features are not in direct contact but through another feature between them. Moreover, the first feature "on", "above" and "over" the second feature include the first feature being directly above and obliquely above the second feature, or it simply means that the first feature has a higher level than the second feature. The first feature "under", "below", and "underneath" the second feature include the first feature directly above and diagonally above the second feature, or it simply means that the first feature has a smaller level than the second feature.

The following disclosure provides many different implementations or examples for implementing different structures of the embodiments of the present disclosure. In order to simplify the disclosure of the embodiments of the present disclosure, the components and configurations of specific examples are described below. Of course, they are only examples, and are not intended to limit the embodiments of the present disclosure. In addition, the embodiments of the present disclosure may repeat reference numerals and/or reference letters in different examples, such repetition is for the purpose of simplification and clarity, and does not indicate the relationship between the various implementations and/or configurations discussed.

The embodiments of the present disclosure will be described in detail below with reference to the accompanying drawings.

Embodiment 1

Please refer to FIG. 1-FIG. 8, in order to solve the problem that the existing vascular stent cannot well adapt to the requirements of the vessels with large deformation during movement, such as the lower extremity arteries, this embodiment provides a peripheral vascular stent comprising a plurality of scaffolding holding units 1 and a membrane 2.

Figure 2:
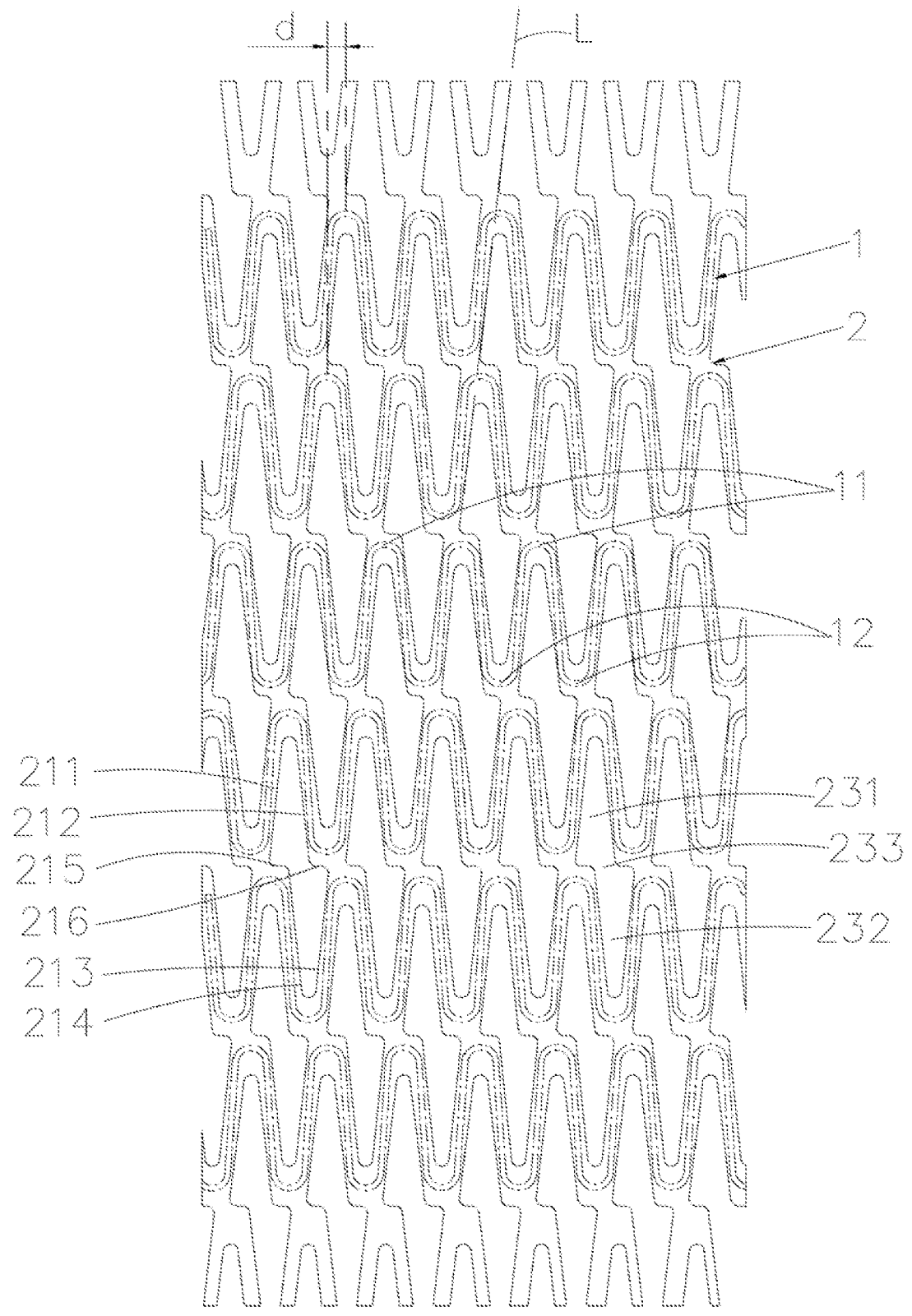
FIG. 2 is a schematic structure diagram of the vascular stent provided in Embodiment 1 of the present disclosure that is split along the axial direction and spread into a plane.

As shown in FIGS. 1 and 2, the plurality of scaffolding holding units 1 are sequentially spaced apart along the axial direction of the peripheral vascular stent. Each scaffolding holding unit 1 is formed of a wire and is in a closed loop shape, where the wire can be a monofilament made by cutting and shaping a pipe or by other forms, or it can be a single wire made by twisting and braiding a plurality of wires, the material of the wire includes, but is not limited to, stainless steel, memory alloy, titanium alloy, tantalum alloy, cobalt-chromium alloy, biodegradable metal, biodegradable polymer, magnesium alloy, pure iron or combinations thereof, and the scaffolding holding units formed by the wire may be self-expanding scaffolding holding units, or a scaffolding holding unit that needs to be expanded with the aid of a balloon or the like; preferably, the wire is made of nickel-titanium alloy, which can realize self-expansion and thus can provide better support force.

Each of the scaffolding holding units 1 comprises a plurality of peaks 11 and valleys 12 taking the axis line of the peripheral vessel stent as the axis and regularly arranged in the circumferential direction, with two adjacent peaks forming a cycle. Wherein, the shape of the wire constituting one cycle only needs to be a shape with a peak and a valley, including but not limited to V-shaped, U-shaped, and the like. The axis of each scaffolding holding unit 1 coincides with the axis of the peripheral vascular stein. In order to adapt to the tapered structure of the lower extremity arteries, the inner diameter of the plurality of scaffolding holding units 1 in the expanded state is tapered from one end to the other end, so as to meet the physiological characteristics of the lower extremity arteries of the human body with a tapered diameter, effectively increase the attached area of the vascular stent to the blood vessel, and reduce the chronic external expansion force of the stent, thereby avoiding the probability of in-stent restenosis.

As shown in FIG. 1 and FIG. 2, the plurality of scaffolding holding units 1 are connected by the membrane 2 covering the scaffolding holding units 1, the flexibility of the membrane 2 is greater than that of the scaffolding holding units 1, so that the peripheral vascular stent adopts flexible connection without fatigue damage in the metal connection structure, and the flexible structure has little irritation to endothelial cells during the process of shortening, torsion, bending, stretching, etc., thereby reducing vascular injury and meeting the shortening rate of the arteries in various deformed states. The material of the membrane 2 includes, but is not limited to, polytetrafluoroethylene, polyether block amide, polyimide, bioabsorbable medical materials, and combinations, preferably, the membrane 2 is polytetrafluoroethylene microporous membrane (ePTFE).

Figure 8:
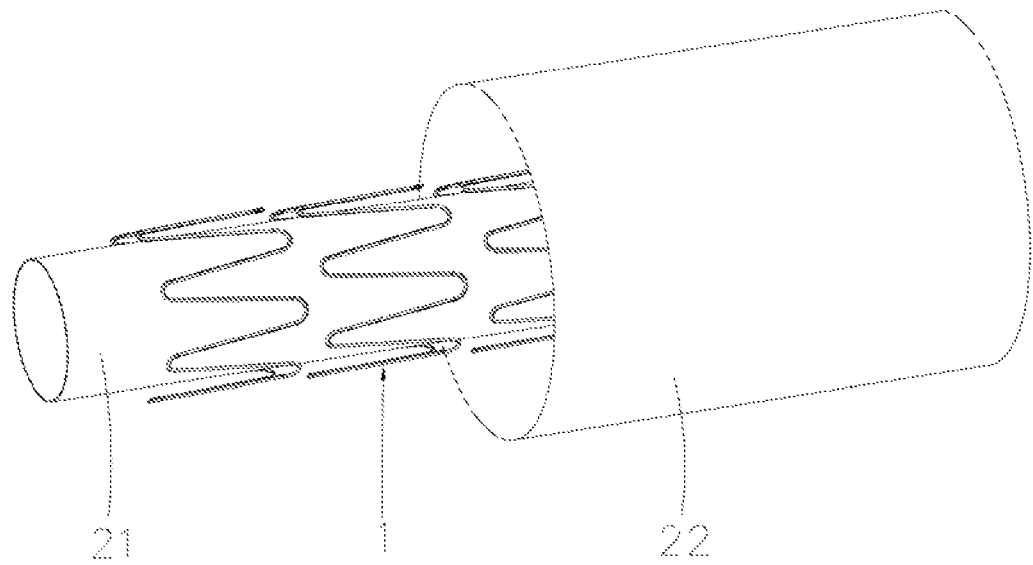
FIG. 8 is a schematic diagram of the vascular stent of Embodiment 1 during the preparation process.

Wherein, the membrane 2 may be a single-layer membrane or a double-layer membrane. When the membrane 2 is a single-layer membrane, the membrane 2 can be arranged on the inner side of the scaffolding holding units 1 to minimize the influence of the peripheral vascular stent on blood flow; the membrane 2 may also be arranged on the outer side of the scaffolding holding units 1 to increase the contact area of the peripheral vascular stent and the vascular wall, and reduce the injury of the peripheral vascular stent to the vascular wall. In this embodiment, the membrane 2 is a double-layer membrane, that is, as shown in FIG. 8, the membrane 2 comprises an inner membrane 21 located on the inner side of the scaffolding holding units 1 and an outer membrane 22 located on the outer side of the scaffolding holding units 1, which can not only reduce the influence of the peripheral vascular stent on blood flow, but also reduce the injury of the peripheral vascular stent to the vascular wall.

Figure 3:
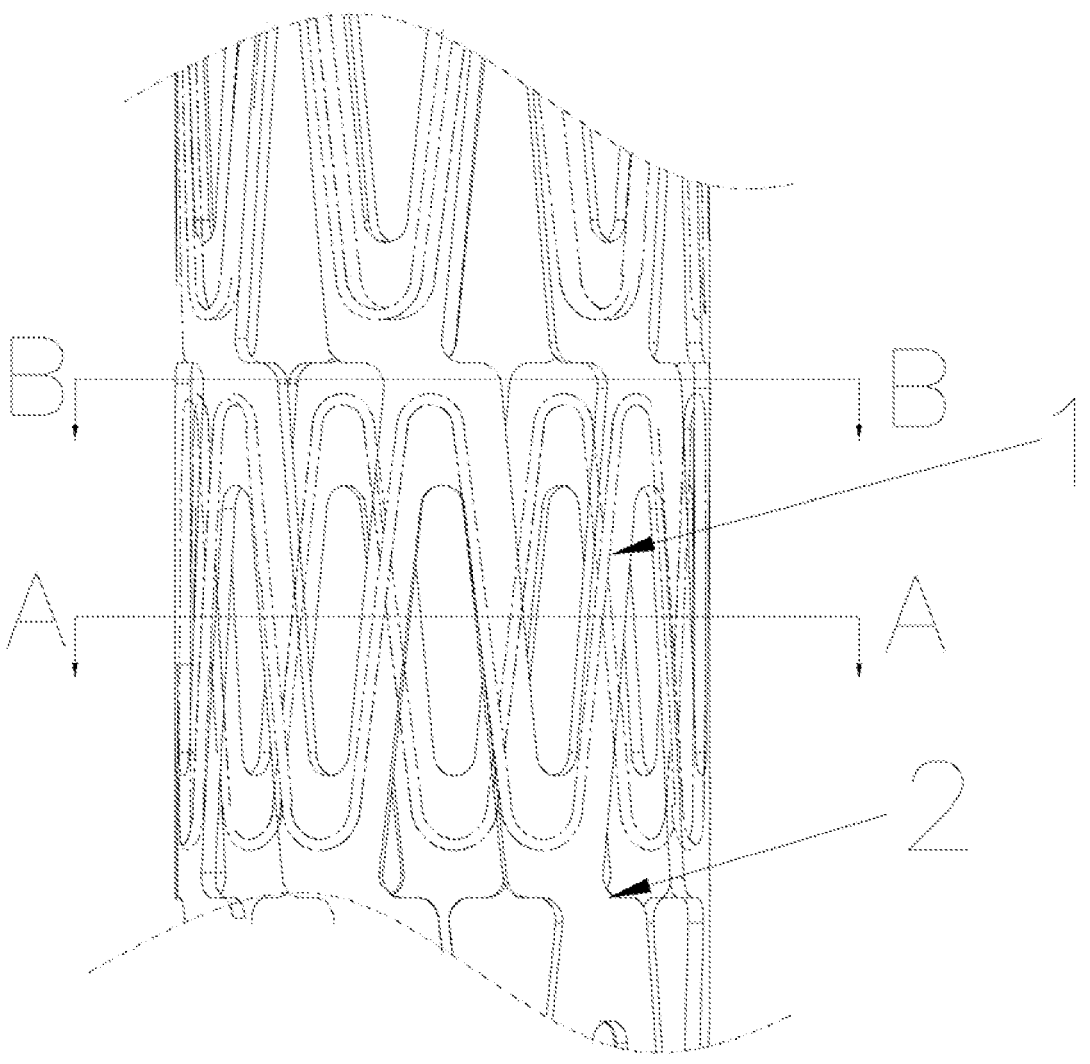
FIG. 3 is a partial enlarged view of the vascular stent provided in Embodiment 1 of the present disclosure.

In order to enable better bending and twisting of the peripheral vascular stent, a plurality of hollowed-out areas 23 are provided on the membrane 2 between the wire of the same scaffolding holding unit 1 and/or between two adjacent scaffolding holding units 1, so that the hollowed-out areas 23 can provide an avoidance space when the vascular stent is bent or twisted. In this embodiment, as shown in FIGS. 1 to 3, the hollowed-out areas 23 are opened between the wire of the same scaffolding holding unit 1 and on the membrane 2 between two adjacent scaffolding holding units 1. The scaffolding holding units 1 are wrapped inside the membrane 2, while there is no scaffolding holding unit 1 extending out the hollowed-out areas 23 and the scaffolding holding units 1 do not directly contact the vascular wall, preferably, the area of the hollowed-out areas 23 is provided as large as possible.

Specifically, between two adjacent scaffolding holding units 1, one scaffolding holding unit 1 and the other scaffolding holding unit 1 are staggered on the circumferential surface (peak staggering), and the staggered distance d is less than one-half cycle, preferably, the staggered distance d is less than or equal to a quarter of the cycle. In this embodiment, as shown in FIG. 2, the staggered distance d is a quarter of the cycle. Moreover, when the cross-section of the vascular stent as shown in FIG. 1 is taken as the circumferential surface, and the circumferential surface is viewed downward according to the orientation in FIG. 1, the clockwise direction is the same as the clockwise rotation direction; in the clockwise direction, each scaffolding holding unit 1 is staggered on the circumferential surface with the same distance from the adjacent scaffolding holding unit 1, of course, those skilled in the art can expect that the vascular stent obtained by the solution "in the counterclockwise direction, each scaffolding holding unit 1 is staggered on the circumferential surface with the same distance from the adjacent scaffolding holding unit 1" can achieve the same effect. In order to more clearly illustrate the staggered structure between two adjacent scaffolding holding units 1, as shown in FIG. 2, when the peripheral vascular stent is split along its axial direction and spread into a plane, the next scaffolding holding unit 1 is always offset to the left by the same distance from the previous scaffolding holding unit 1, so that the peak tops and peak tops, valley bottoms and valley bottoms, and peak tops and valley bottoms of two adjacent scaffolding holding units are not aligned in the axial direction.

Specifically, as shown in FIG. 2, each hollowed-out area 23 in this embodiment includes first hollowed-out portions 231 located in the peaks 11 of each scaffolding holding unit 1, and second hollowed-out portions 231 located in the valleys 12 of each scaffolding holding unit 1, and third hollowed-out portions 233 located between two adjacent scaffolding holding units 1 and respectively in communication with the first hollowed-out portions 231 and the second hollowed-out portions 232. And, each of the third hollowed-out portions 233 is only in communication with the nearest first hollowed-out portion 231 and second hollowed-out portion 232, and the respective hollowed-out portions 23 are mutual independent and are not in communication with each other, such that between two adjacent scaffolding holding units, the valley bottoms of one scaffolding holding unit 1 and the nearest peak tops of the other scaffolding holding unit 1 are only connected by strip-shaped membranes 2.

Further, the first hollowed-out portions 231 are surrounded by first walls 211 and second walls 212 connected by upper ends thereof, and the second hollowed-out portions 232 are surrounded by third walls 213 and fourth walls 214 connected by lower ends thereof, and the third hollowed-out portions 233 are surrounded by fifth walls 215 respectively connected to the lower ends of the first walls 211 and the upper ends of the fourth walls 214, and sixth walls 216 respectively connected to the lower ends of the second walls 212 and the upper ends of the third walls 213. The first walls 211 and the third walls 213 are parallel, the second walls 212 and the fourth walls 214 are parallel; the first walls 211 are parallel to each other, and the second walls 212 are parallel to each other, and the angles between the first walls 211 and the second walls 212 are acute angles. As shown in FIG. 2, when the peripheral vascular stent is split along its axial direction and spread into a plane shape, two nearest first walls 211 of two adjacent scaffolding holding units 1 are on a first straight line L, and the first straight line L is arranged obliquely, that is to say, the first straight line L intersects the length direction of the peripheral vascular stent. The staggering arrangement of the scaffolding holding units 1 and the structure design of the hollowed-out areas 23 cause the peripheral vascular stent can form a spiral-like structure, so that the peripheral vascular stent can better maintain the circular cross-section of the vascular stent in the state of bending, torsion, etc., and avoid the collapse of the vascular stent; moreover, this structure design cause the peripheral vascular stent has better flexibility and radial support property while having better bending, torsion, axial compression and stretching properties.

The method for preparing the peripheral vascular stent of this embodiment was:

The inner membrane 21 and the outer membrane 22 were respectively arranged on the inner side and outer side of the scaffolding holding units 1, and heated them to wrap the scaffolding holding units 1 between the inner membrane 21 and the outer membrane 22, the inner membrane 21 and the outer membrane 22 beyond the scaffolding holding units 1 are thermally melt to form into an integral membrane 2, then the plurality of hollowed-out areas 23 were opened on the inner membrane 21 and the outer membrane 22; or, the plurality of hollowed-out areas 23 were respectively opened on the inner membrane 21 and the outer membrane 22, then the inner membrane 21 and the outer membrane 22 were respectively arranged on the inner side and outer side of the scaffolding holding units 1, the hollowed-out areas 23 on the inner membrane 21 was aligned with the hollowed-out areas 23 on the outer membrane 22, the scaffolding holding units 1 were wrapped between the inner membrane 21 and the outer membrane 22 by heating, and the inner membrane 21 and the outer membrane 22 beyond the scaffolding holding units 1 are thermally melt to form into an integral membrane 2.

In this embodiment, the outer surface of the inner membrane 21, the outer surface of the outer membrane 22 and the face between the inner membrane 21 and the outer membrane 22 may selectively coated with drugs, thereby greatly increasing the drugs attachment area and methods, and the coated drugs include, but are not limited to, drug polymers carriers or active agents (such as biologically active agents), and topically administrated therapeutic substances, to achieve anti-vascular proliferation and anti-endothelialization.

Embodiment 2 and Embodiment 3

The two embodiments are basically the same as Embodiment 1, the only differences are: the membrane 2 of Embodiment 2 is a single-layer membrane arranged on the inner side of the scaffolding holding units 1, and the membrane 2 of Embodiment 3 is a single-layer membrane arranged on the outer side of the scaffolding holding units 1.

The method for preparing the peripheral vascular stents of these two embodiments was:

The membrane 2 and the scaffolding holding units 1 were fixed by thermally melting, seaming, and the like, then the plurality of hollowed-out areas 23 were opened on the membrane 2; or the plurality of hollowed-out areas 23 were opened on the membrane 2, then the membrane 2 and the scaffolding holding units 1 were fixed by thermally melting, seaming, and the like.

The peripheral vascular stent has an expanded state and a contracted state, and has a larger inner diameter in the expanded state than that in the contracted state. The structures of the peripheral vascular stents of the above-mentioned Embodiments 1 to 3 are described when the peripheral vascular stent is in the expanded state.

The three peripheral vascular stents of the three embodiments are stored in a delivery mechanism and are in a contracted state during delivery into the blood vessel, and when delivered to the desired part of the blood vessel, after the delivery mechanism is retracted, the peripheral vascular stents are automatically expanded to the expanded state to support the blood vessel.

The plurality of independent scaffolding holding units 1 in the vascular stent of the present disclosure are connected through the flexible membrane 2 with the hollowed-out areas 23, and in the first aspect, the flexible structural connection has no fatigue damage existing in the metal connection structure, and the flexible structure is less irritating to endothelial cells during the shortening process, thereby reducing vascular injury, and can adapt to the shortening rates of the artery in various deformed states; in the second aspect, the provision of the hollowed-out areas 23 allows the vascular stent of the present disclosure to adapt to the deformation of the peripheral vessels under torsion, and the flexible structure has little irritation to endothelial cells during the torsion process, thereby reducing vascular injury; in the third aspect, the vascular stent of the present disclosure has no "fish-scale phenomenon" or fatigue damage in the metal stent in the bending state, especially in the peripheral vessels of the hip joint (such as the popliteal artery, etc.), and the present disclosure can achieve bending under a small radius of curvature without injuring the vascular endothelium; in the fourth aspect, the provision of the flexible connection allows the vascular stent of the present disclosure to have a sufficient axial stretching rate to meet the axial stretching deformation of the peripheral vessels; and in the fifth aspect, the plurality of closed annular scaffolding holding units 1 arranged at intervals in the axial direction can provide sufficient radial support force, and can withstand the radial force and collapse or pinch load of peripheral vessels, and effectively support the artery to provide sufficient blood flow.

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A peripheral vascular stent, having an expanded state and a contracted state, the peripheral vascular stent having a larger inner diameter in the expanded state than that in the contracted state; wherein, the peripheral vascular stent comprises: scaffolding holding units, the scaffolding holding units are a plurality of scaffolding holding units arranged at intervals along an axial direction of the peripheral vascular stent, each of the scaffolding holding units is formed of a wire and is in a closed ring shape, and each of the scaffolding holding units comprises a plurality of peaks and valleys regularly arranged in the circumferential direction, with two adjacent peaks forming a cycle; a membrane, the membrane is covered on the plurality of scaffolding holding units, the flexibility of the membrane is greater than that of the scaffolding holding units, the membrane between the wires of the same scaffolding holding unit and/or between two adjacent scaffolding holding units is provided with a plurality of openings; the openings comprise: first openings located within the peaks of each scaffolding holding unit, second openings located within the valleys of each scaffolding holding unit, a plurality of third openings located between two adjacent scaffolding holding units and in communication with the first openings and the second openings respectively, wherein each of the third openings is mutually independent and only in communication with the nearest first openings and the nearest second openings; two adjacent scaffolding holding units are only connected by the membrane beyond the openings and without metal connection; between two adjacent scaffolding holding units, one scaffolding holding unit and the other scaffolding holding unit are staggered on a circumferential surface, and a staggered distance between the nearest two peaks in the adjacent scaffolding holding units is less than one-half cycle; between two adjacent scaffolding holding units, the valley bottoms of one scaffolding holding unit and the nearest peak tops of the other scaffolding holding unit are only connected by strip-shaped membranes; wherein in a clockwise direction, each of the scaffolding holding units and the adjacent scaffolding holding unit are staggered on the circumferential surface and the staggered distance between any two adjacent scaffolding holding units is the same.

2. The peripheral vascular stent according to claim 1, wherein, the staggered distance is less than or equal to a quarter of the cycle.

3. The peripheral vascular stent according to claim 1, wherein, an axis of each scaffolding holding unit coincides with an axis of the peripheral vascular stent.

4. The peripheral vascular stent according to claim 1, wherein, the first openings are surrounded by first walls and second walls connected by upper ends thereof, and the second openings are surrounded by third walls and fourth walls connected by lower ends thereof, the third openings are surrounded by fifth walls respectively connected to the lower ends of the first walls and the upper ends of the fourth walls, and sixth walls respectively connected to the lower ends of the second walls and the upper ends of the third walls.

5. The peripheral vascular stent according to claim 4, wherein, when the peripheral vascular stent is split along its axial direction and spread into a plane shape, two nearest first walls of two adjacent scaffolding holding units are on a first straight line.

6. The peripheral vascular stent according to claim 4, wherein, angles between the first walls and the second walls are acute angles.

7. The peripheral vascular stent according to claim 4, wherein, when the peripheral vascular stent is split along its axial direction and spread into a plane shape, the first walls and the third walls are parallel, the second walls and the fourth walls are parallel, and a plurality of second walls are parallel.

8. The peripheral vascular stent according to claim 1, wherein, the membrane is wrapped on an outer side and/or an inner side of the scaffolding holding units.

9. The peripheral vascular stent according to claim 1, wherein, the membrane comprises an inner membrane located on the inner side of the scaffolding holding units and an outer membrane located on the outer side of the scaffolding holding units, the inner membrane and the outer membrane are fixedly connected, and the scaffolding holding units are wrapped between the inner membrane and the outer membrane.

10. The peripheral vascular stent according to claim 9, wherein, the inner membrane and the outer membrane that are in contact are thermally melted to form the membrane.

11. The peripheral vascular stent according to claim 1, wherein, the inner diameter of the peripheral vessel stent in the expanded state is gradually tapered from one end to the other end.

12. The peripheral vascular stent according to claim 1, wherein, the membrane is coated with drugs.

13. The peripheral vascular stent according to claim 1, wherein, a material used for the scaffolding holding units is selected from the group consisting of stainless steel, memory alloy, titanium alloy, tantalum alloy, cobalt-chromium alloy, biodegradable metal, biodegradable polymer, magnesium alloy, pure iron, and combinations thereof.

14. The peripheral vascular stent according to claim 13, wherein, the material of the scaffolding holding units is nickel-titanium alloy.

15. The peripheral vascular stent according to claim 1, wherein, a material used for the membrane is selected from the group consisting of polytetrafluoroethylene, polyether block amide, polyimide, bioabsorbable medical materials, and combinations thereof.

16. The peripheral vascular stent according to claim 1, wherein, the membrane is polytetrafluoroethylene microporous membrane.

17. A method for preparing a peripheral vascular stent according to claim 1, wherein, fixing the membrane and the scaffolding holding units with each other, and then opening a plurality of openings on the membrane; or opening a plurality of openings on the membrane, and then fixing the membrane and the scaffolding holding units with each other; or respectively arranging an inner membrane and an outer membrane on the inner side and outer side of the scaffolding holding units, wrapping the scaffolding holding units between the inner membrane and the outer membrane by heating the inner membrane and the outer membrane, thermally melting the inner membrane and the outer membrane beyond the scaffolding holding units to form into an integral membrane, and then opening a plurality of openings on the membrane; or respectively opening a plurality of openings on an inner membrane and an outer membrane, then respectively arranging the inner membrane and the outer membrane on the inner side and outer side of the scaffolding holding units, aligning the openings on the inner membrane with the openings on the outer membrane to form the third openings that are mutually independent, wrapping the scaffolding holding units between the inner membrane and the outer membrane by heating, and thermally melting the inner membrane and the outer membrane beyond the scaffolding holding units to form into an integral membrane.

18. A method for treating peripheral artery disease, the method comprising placing the peripheral vascular stent according to claim 1 into a peripheral artery.

* * * * *